(12) United States Patent
Cook et al.

(10) Patent No.: US 11,596,780 B2
(45) Date of Patent: Mar. 7, 2023

(54) CONTROLLED OUTGASSING OF HYBERBARICALLY LOADED MATERIALS FOR THE DELIVERY OF OXYGEN AND OTHER THERAPEUTIC GASES IN BIOMEDICAL APPLICATIONS

(71) Applicant: THE JOHNS HOPKINS UNIVERSITY, Baltimore, MD (US)

(72) Inventors: Colin Cook, Baltimore, MD (US); Warren Grayson, Reisterstown, MD (US)

(73) Assignee: The Johns Hopkins University, Baltimore, MD (US)

( * ) Notice: Subject to any disclaimer, the term of this patent is extended or adjusted under 35 U.S.C. 154(b) by 190 days.

(21) Appl. No.: 14/893,115

(22) PCT Filed: May 28, 2014

(86) PCT No.: PCT/US2014/039806
§ 371 (c)(1),
(2) Date: Nov. 23, 2015

(87) PCT Pub. No.: WO2014/193963
PCT Pub. Date: Dec. 4, 2014

(65) Prior Publication Data
US 2016/0114145 A1 Apr. 28, 2016

Related U.S. Application Data

(60) Provisional application No. 61/828,126, filed on May 28, 2013.

(51) Int. Cl.
| | | |
|---|---|---|
| *A61M 37/00* | (2006.01) | |
| *A61M 16/12* | (2006.01) | |
| *A61L 27/56* | (2006.01) | |
| *A61L 27/52* | (2006.01) | |
| *A61L 27/38* | (2006.01) | |
| *A61L 27/54* | (2006.01) | |
| *A61K 9/113* | (2006.01) | |
| *C12N 5/077* | (2010.01) | |

(52) U.S. Cl.
CPC ......... *A61M 37/0069* (2013.01); *A61K 9/113* (2013.01); *A61L 27/38* (2013.01); *A61L 27/52* (2013.01); *A61L 27/54* (2013.01); *A61L 27/56* (2013.01); *A61M 16/12* (2013.01); *C12N 5/0653* (2013.01); *A61L 2300/114* (2013.01); *A61L 2300/404* (2013.01); *A61M 2202/0208* (2013.01); *A61M 2202/0216* (2013.01); *A61M 2202/0233* (2013.01); *A61M 2202/0275* (2013.01); *A61M 2202/0291* (2013.01); *A61M 2207/10* (2013.01)

(58) Field of Classification Search
CPC ...... A61M 37/0069; A61M 2202/0291; A61M 2202/0216; A61M 2202/0208; A61M 2202/0275; A61M 2207/10; A61M 16/12; A61M 2202/0233; A61K 9/113; A61L 27/38; A61L 27/54; A61L 27/52; A61L 27/56; A61L 2300/114; A61L 2300/404; C12N 5/0653
See application file for complete search history.

(56) References Cited

U.S. PATENT DOCUMENTS

| | | | |
|---|---|---|---|
| 4,842,620 A | 6/1989 | Hammel et al. | |
| 5,766,317 A | 6/1998 | Cable et al. | |
| 7,105,151 B2 | 9/2006 | Unger et al. | |
| 2003/0120204 A1* | 6/2003 | Unger | A61K 41/0028 604/82 |
| 2003/0190367 A1* | 10/2003 | Balding | 424/549 |
| 2004/0101740 A1 | 5/2004 | Sanders et al. | |
| 2004/0213998 A1 | 10/2004 | Hearley et al. | |
| 2006/0030483 A1 | 2/2006 | Jang | |
| 2009/0211399 A1 | 8/2009 | Mohtadi et al. | |

FOREIGN PATENT DOCUMENTS

WO 2009/018269 A1 2/2009

OTHER PUBLICATIONS

Oh et al. Biomaterials 30 (2009) 757-762.*
Oh et al. "Oxygen generating scaffolds for enhancing engineered tissue survival" Biomaterials 30 (2009) 757-762.*

* cited by examiner

*Primary Examiner* — Satyendra K Singh
(74) *Attorney, Agent, or Firm* — Casimir Jones, S.C.; Jeffrey W. Childers

(57) ABSTRACT

Devices and methods for delivering oxygen and other therapeutic gases to a target, such as a tissue, a tissue-engineered construct, and a wound, in a controlled and sustained manner are disclosed.

6 Claims, 9 Drawing Sheets

CONTROLLED OUTGASSING OF HYBERBARICALLY LOADED MATERIALS FOR THE DELIVERY OF OXYGEN AND OTHER THERAPEUTIC GASES IN BIOMEDICAL APPLICATIONS

REFERENCE TO RELATED APPLICATIONS

This application is a 35 U.S.C. § 371 National Stage Entry of International Application No. PCT/US14/39806 having an international filing date of May 28, 2014, which claims the benefit of U.S. Provisional Application No. 61/828,126, filed May 28, 2013, the content of each of the aforementioned applications is herein incorporated by reference in its entirety.

BACKGROUND

Oxygen delivery remains one of the greatest challenges in tissue engineering. Consequently, many technologies and approaches have been developed, but each has met with limited success. For example, perfluorocarbons are liquids that have a high oxygen solubility (upwards of 50% V/V) and are used as blood supplements filling a role similar to hemoglobin. In non-circulatory applications, however, their oxygen capacity is at most the amount of oxygen contained in their volume at atmospheric pressures. Thus, they make poor oxygen storage materials and release the oxygen too quickly. They also are relatively expensive.

Peroxides, such as calcium peroxide, have a high oxygen capacity and are able to decompose in the presence of water to release oxygen. Decomposition of the peroxides results in the production of reactive oxygen species, which are a general concern with this approach.

The levels of oxygen in the circulatory system of a patient can be increased by exposing the patient to elevated oxygen partial pressures, for example, in a hyperbaric chamber. This increase, however, is only therapeutic to tissues with functional vasculature. The treatment is systemic and not localized. Further, this treatment regimen requires that the patient be confined to a small chamber for extended periods of time, making it undesirable for many patients.

Prevascularization is another technique for improving blood supply, and thus oxygen supply, to engineered tissues. Prevascularization, however, requires significant in vitro cultivation, limiting its clinical translatability. Further, prevascularization requires significant development before it can be applied to large defects.

SUMMARY

In some embodiments, the presently disclosed subject matter provides a microtank for delivering one or more gases in a controlled and sustained manner, the microtank comprising one or more vessels, wherein the one or more vessels have a volume defined by at least one gas barrier and/or a means for mechanical confinement, wherein the volume of the one or more vessels is capable of being loaded, at atmospheric or hyperbaric pressures, with one or more gases and subsequently releasing the one or more gases in a controlled and sustained manner.

In other aspects, the presently disclosed subject matter provides a method for fabricating a microtank for delivering one or more gases in a controlled and sustained manner, the method comprising: (a) providing or preparing one or more vessels, wherein the one or more vessels have a volume defined by at least one gas barrier and/or a means for mechanical confinement, wherein the volume of the one or more vessels is capable of being loaded, at atmospheric or hyperbaric pressures, with one or more gases and subsequently releasing the one or more gases in a controlled and sustained manner; and loading the one or more vessels with one or more gases.

In yet other aspects, the presently disclosed subject matter provides a method for delivering one or more gases to a target in a controlled and sustained manner, the method comprising: (a) providing a microtank comprising one or more vessels, wherein the one or more vessels have a volume defined by at least one gas barrier and/or a means for mechanical confinement, wherein the volume of the one or more vessels is capable of being loaded, at atmospheric or hyperbaric pressures, with one or more gases and subsequently releasing the one or more gases in a controlled and sustained manner; (b) loading the one or more vessels with one or more gases; and (c) releasing the one or more gases to the target in a controlled and sustained manner.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
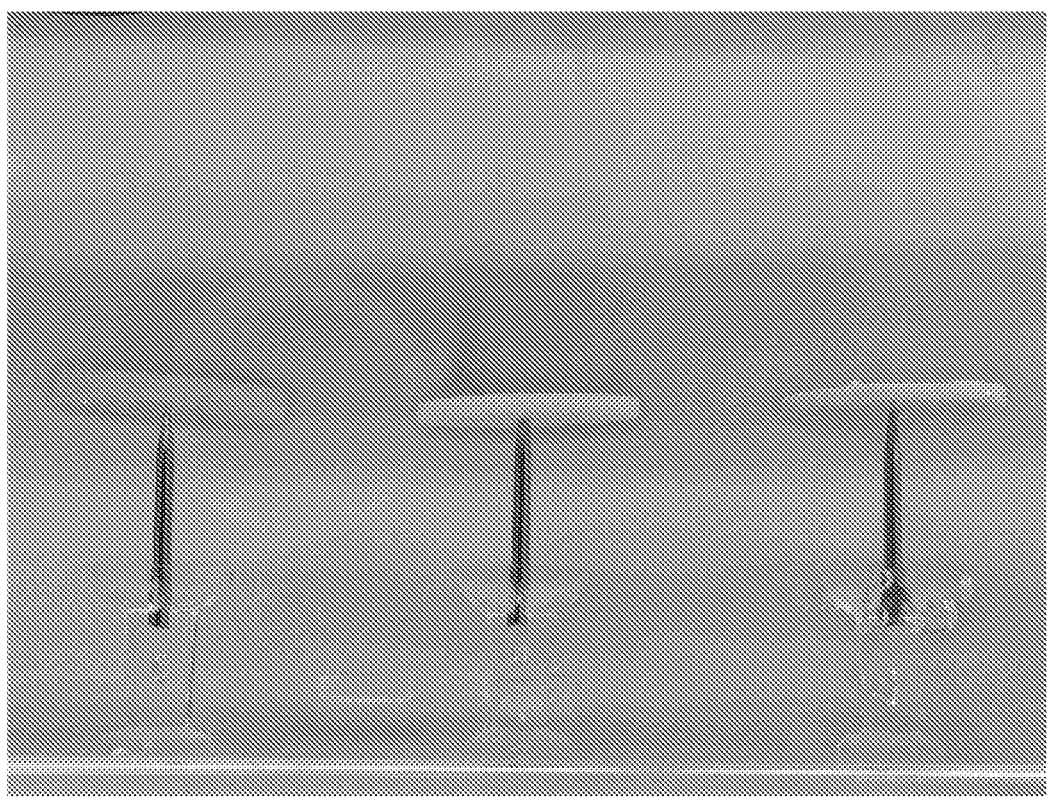
Figure 2:
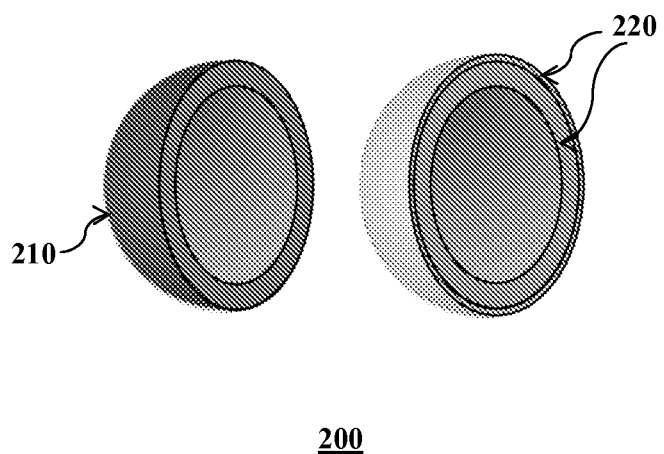
Figure 3:
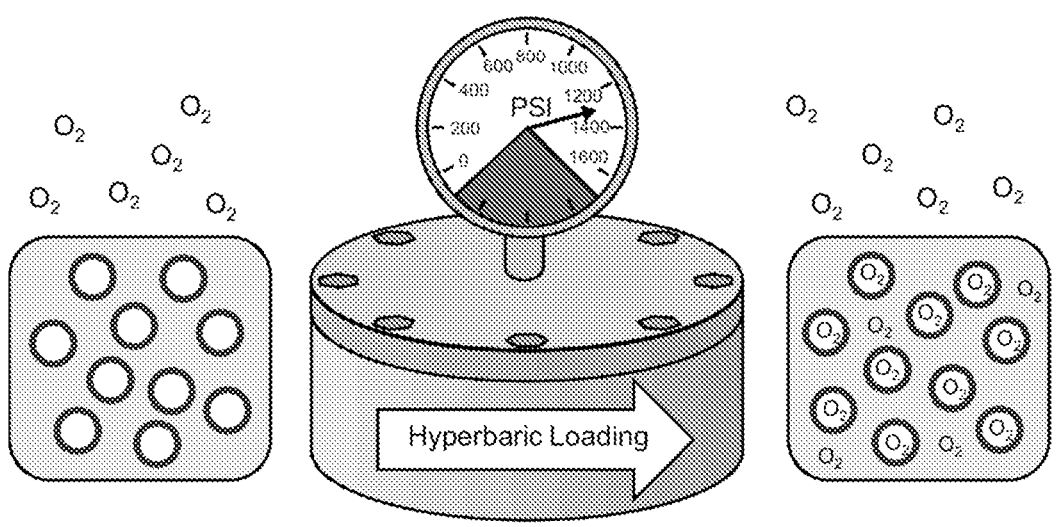
Figure 4:
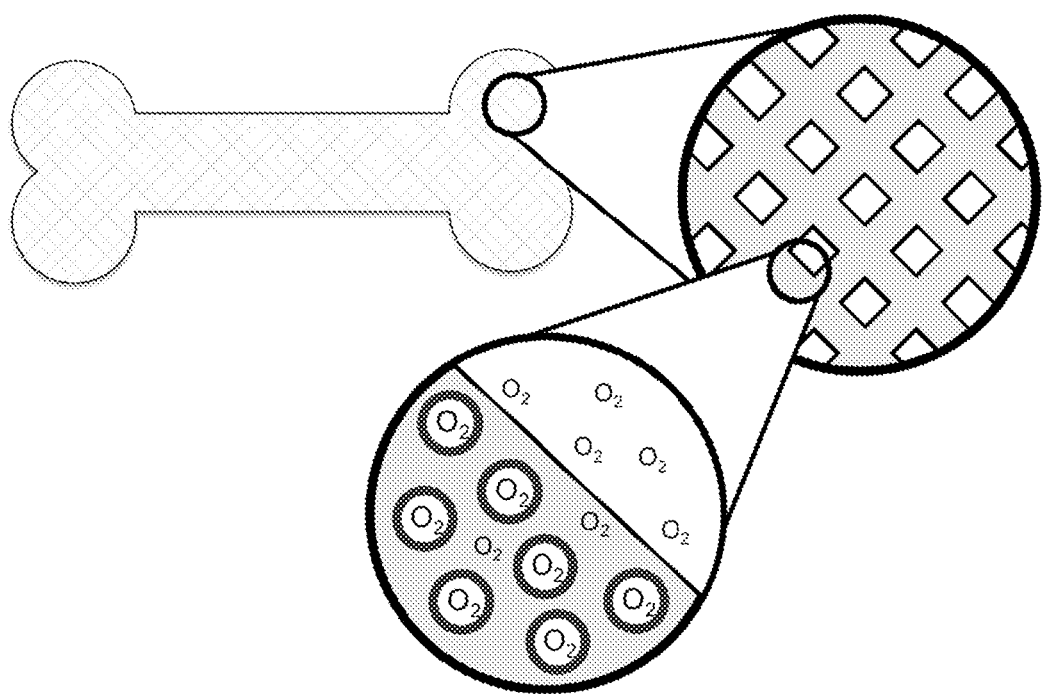
Figure 5:
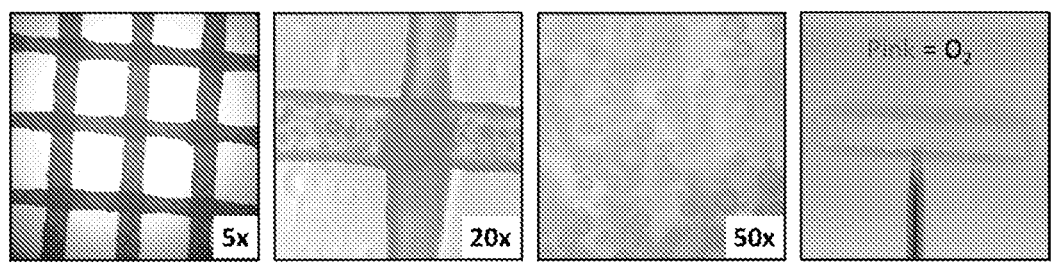
Figure 6:
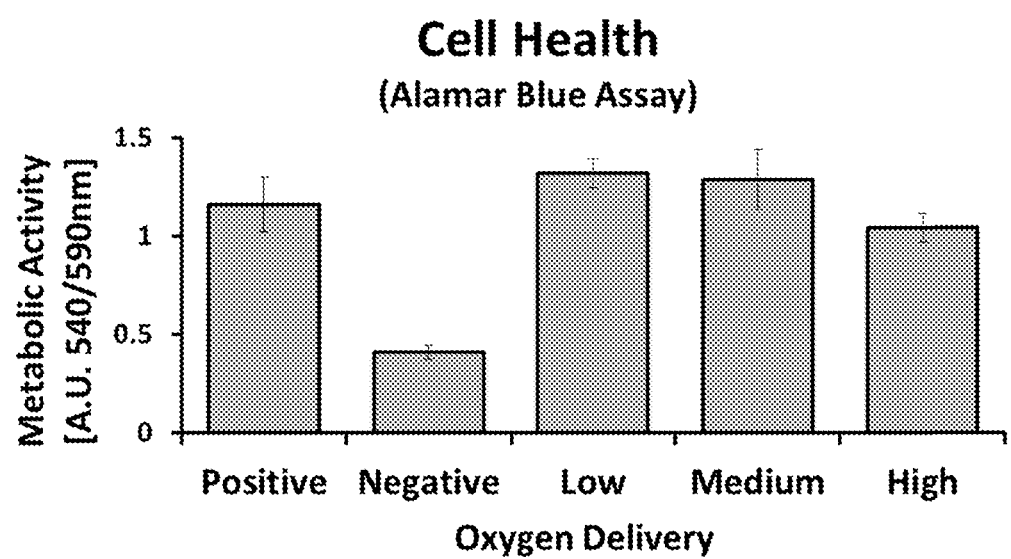
Figure 7:
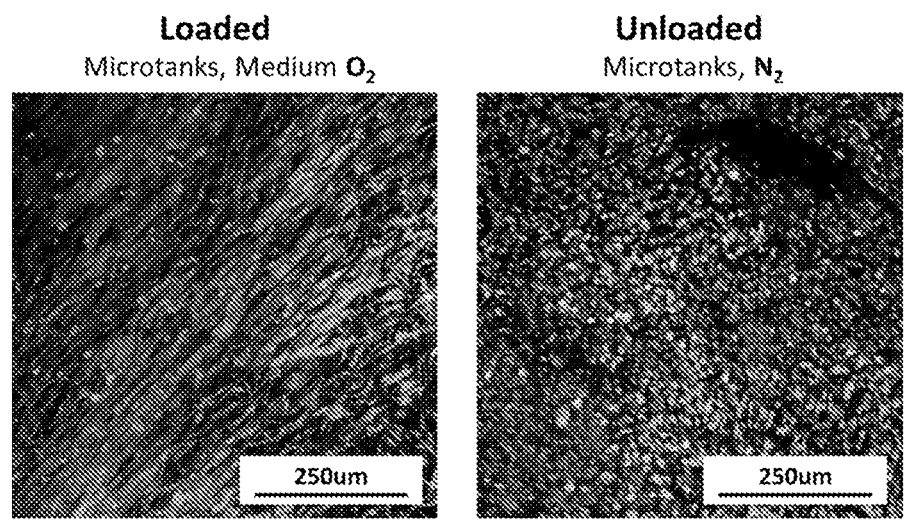
Figure 8:
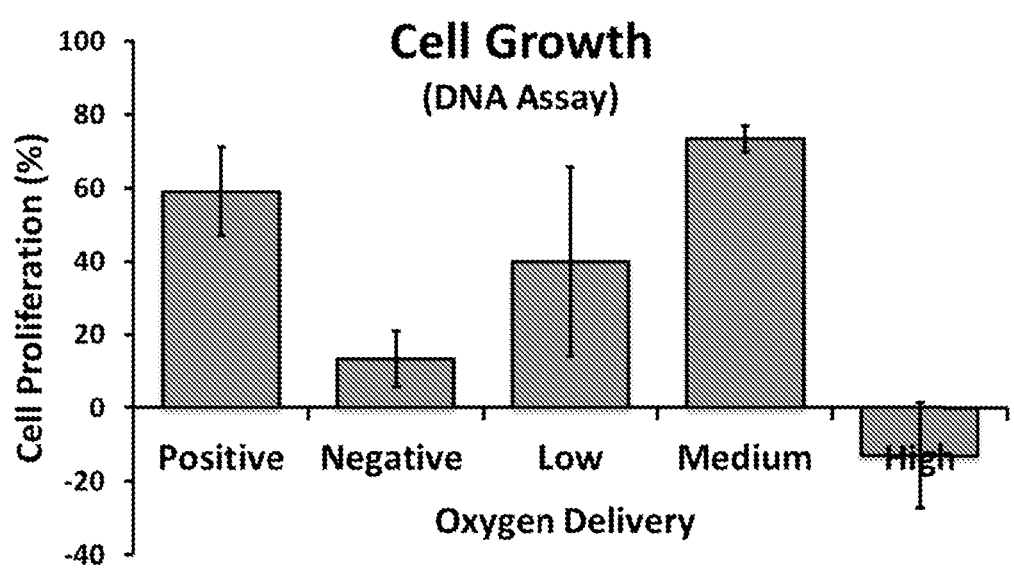
Figure 9A:
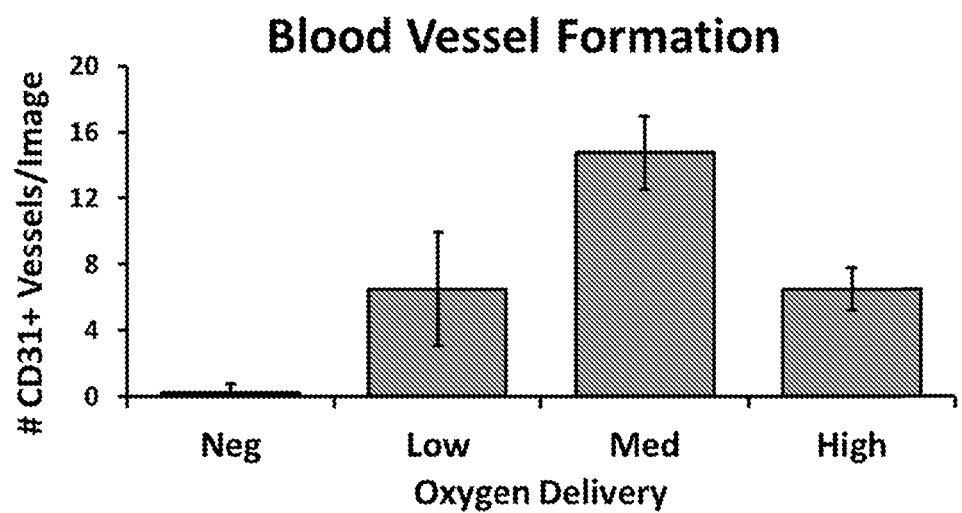
Figure 9B:
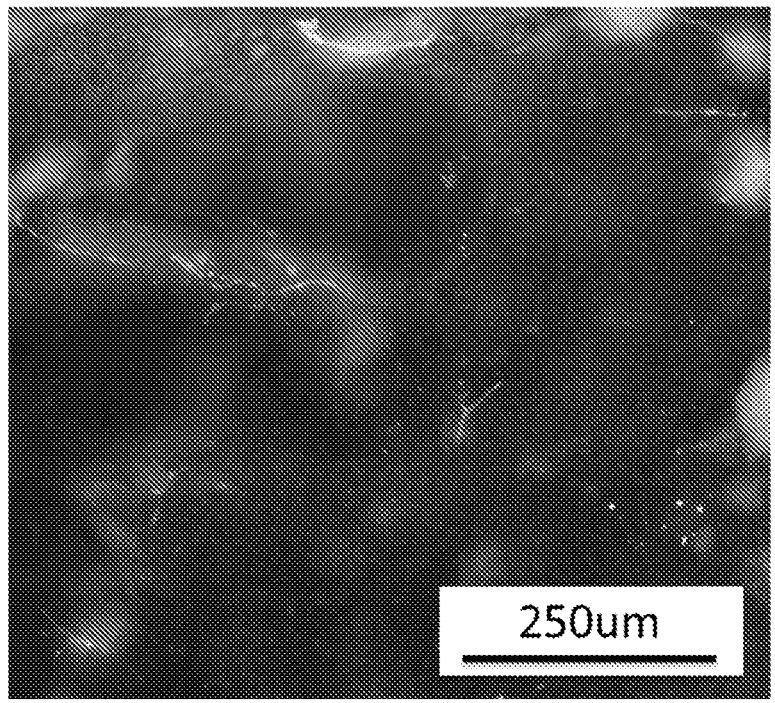

Having thus described the presently disclosed subject matter in general terms, reference will now be made to the accompanying Figures, which are not necessarily drawn to scale, and wherein:

FIG. 1 shows photographs of oxygen releasing scaffolds in resazurin solution with pink indicating the presence of oxygen (visible at liquid surface exposed to air and around scaffolds);

FIG. 2 is a depiction of the presently disclosed microtanks 200 with a single gas barrier 210 (left) or multiple gas barrier layers 220 (right);

FIG. 3 shows a process for loading a presently disclosed microtank with gas and subsequent outgassing;

FIG. 4 illustrates an application of the presently disclosed subject matter to bone tissue engineering scaffolds comprising a PCL phase and a hydrogel phase, whereby the presently disclosed microtanks are embedded in the PCL phase and oxygen outgasses into the hydrogel phase;

FIG. 5 shows 3D printed microtanks and release of oxygen from microtank-containing scaffolds (far right);

FIG. 6 shows the results of an Alamar blue assay demonstrating that normative cell metabolism can be maintained in anoxic environments through microtank oxygen supply;

FIG. 7 shows live (light gray)/Dead (dark gray) fluorescence images highlighting the ability of microtank oxygen augmentation to maintain cell viability in anoxic environments. Note the healthy, elongated morphology (left) versus the dying, balled up morphology (right);

FIG. 8 shows that quantification of changes in DNA highlight the ability of microtanks to enable robust cell expansion within anoxic environments. It is important to match delivery rates to cellular demand for optimal benefit; and FIGS. 9A and 9B shows that immunostaining of blood vessel marker CD31 demonstrates significantly greater vessel formation with microtank oxygen augmentation (A).

Vessels can be seen sprouting throughout the fibrin gel (B), which is critical for the long term viability of the graft.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter provides devices and methods for delivering oxygen and other therapeutic gases in a controlled and sustained manner. The presently disclosed subject matter can be applied to tissue engineering and the mitigation of ischemia and hypoxia, among other applications. The presently disclosed subject matter generally includes the hyperbaric loading of a gas, e.g., oxygen or another therapeutic gas or gases, into nano to micro-scale pressurized vessels, referred to herein as microtanks, through the use of, in some embodiments, a hyperbaric chamber and the subsequent controlled release, or outgassing, of the gas from the microtanks by virtue of their engineered gas barrier properties. By tuning the gas barrier properties of the microtanks, the release of gas theoretically can be sustained over a period of a few minutes to several months, although in practice a sustained release over one to three weeks is appropriate for many applications.

A. Microtanks for Delivering One or More Gases to a Target

The presently disclosed subject matter provides a microtank for delivering one or more gases in a controlled and sustained manner, the microtank comprising one or more vessels, wherein the one or more vessels have a volume defined by at least one gas barrier and/or a means for mechanical support/confinement, wherein the volume of the one or more vessels is capable of being loaded with one or more gases at an atmospheric or a hyperbaric pressure and subsequently releasing the one or more gases in a controlled and sustained manner.

As used herein, the term "microtank" refers to a volume of gas, a vacuum (i.e., a region of space having a low gas pressure relative to its surroundings, e.g., a gas pressure much lower than atmospheric pressure), a liquid, or a solid surrounded by material(s) that act as gas barriers and/or mechanical support/confinement. In some embodiments, the presently disclosed microtanks comprise hollow microspheres having a diameter ranging from about 50 μm to about 100 μm and can be engineered from high-gas-barrier polymers that are capable of being hyperbarically loaded with oxygen. The low intrinsic oxygen permeability of the polymer, which can form the shell of the microtanks, regulates the outward diffusion of oxygen along the pressure differential into the surrounding environment.

The presently disclosed microtanks can provide localized oxygen delivery over, for example, a period ranging from about one weeks to three weeks through controlled permeation of hyperbaric oxygen from hollow core. The presently disclosed provide a high capacity oxygen delivery without toxic reaction products and can be used as an additive product for oxygen supply in TE, ulcers, grafts, and the like.

Referring now to FIG. 2 is a depiction of a representative microtank 200 having a single gas barrier 210 (left) or multiple gas barrier layers 220 (right).

In representative embodiments, the gas barrier and/or means for mechanical support/confinement can comprise a material selected from the group consisting of polyvinyl alcohol (PVOH), ethylene vinyl alcohol (EVOH), polyethylene terephthalate (PET), polycaprolactone (PCL), poly (lactic-co-glycolic acid) (PLGA), poly(lactic acid) (PLA), poly(glycolic acid) (PGA), a biocompatible polymer, a silica coating, a metal coating, a ceramic, and the like, and combinations thereof.

In some embodiments, a microtank can have a dimension on the order of about 1 nanometer to about 1000 micrometers. For example, the presently disclosed microtanks can have at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In yet other embodiments, the microtank has at least one dimension in the range of about one micrometer (μm), i.e., $1 \times 10^{-6}$ meters, to about 1000 μm. One of ordinary skill in the art would appreciate that larger and smaller microtanks are possible and may be suitable for use depending on the application (e.g., on the scale of nanometers or millimeters). For example, the innate pores in some polymers can act as microtanks (e.g. cavitated PET). Microtanks include, but are not limited to, microballoons, hollow microspheres, syntactic foams (i.e., a composite formed by filling a material, e.g., a polymer, metal, or ceramic with hollow particles, or microballoons), emulsions, or otherwise closed-cell structures.

In some embodiments, one or more vessels can have a dimension ranging from about 1 nanometer to about 1000 nanometers. In other embodiments, one or more vessels can have a dimension ranging from about 1 micrometer to about 1000 micrometers.

The presently disclosed subject matter includes two aspects: the loading of the microtanks and the controlled release of gases from the microtanks. Without wishing to be bound to any one particular theory, the presently disclosed subject matter is based, in part, on the ideal gas law, Fick's law, and the gas permeability of materials.

As described by the ideal gas law, the amount of gas within a confined volume is proportional to the pressure of the gas, and can be described by the following equation:

$$PV = nRT$$

wherein P is the pressure of the gas, V is the volume of the gas, n is the amount of gas, which can be expressed as the number of moles of gas, T is the temperature of the gas and R is the ideal or universal gas constant.

Hence, significant gas storage can be achieved in microtanks if the microtanks are loaded to hyperbaric pressures, with larger amounts of gas stored at higher pressures in a constant volume. The maximum loading pressure is limited, in practice, by the mechanical capacity of the microtanks to safely contain the pressure.

Fick's first law of diffusion states that gases will tend to diffuse from regions of higher partial pressures to regions of lower partial pressures. Hence, when initially placed in a hyperbaric chamber, gases will tend to permeate into the microtanks. Upon removal from the hyperbaric chamber, gases will tend to exit the microtanks, i.e., referred to herein as "outgassing."

As a gas leaves a microtank, the driving force for subsequent gas release is reduced, typically resulting in an exponentially decaying release profile. Studies on the permeability of materials to gases have shown that permeability is a function of barrier thickness, material composition, and defect presence, among other parameters. Permeability to gases can range over several orders of magnitude depending on the material choice, allowing the time course of release to span several orders of magnitude, as well.

i. Enhanced Gas Loading of the Microtanks

As provided hereinabove, loading of a gas or gases into the microtanks can be achieved through the use, in some embodiments, of a hyperbaric chamber. Under normal conditions, however, loading times will be comparable to release times, which could be prohibitively long, thereby making loading of the microtanks impracticable. By elevating the temperature of the hyperbaric chamber, however, the loading times can be reduced by orders of magnitude. This characteristic arises because permeation, diffusion, and sorption all exponentially depend on temperature. For example, many relevant polymers exhibit a nearly 10- to 100-fold increase in permeability upon heating from about 37° C. to about 100° C. One of ordinary skill in the art would recognize that the microtanks could be loaded at a temperature ranging from sub-zero to the combustion temperature of the material, e.g., the gas, being used. As used herein, the "combustion temperature" is the temperature at which a reaction between a combustible material and an oxidizer occurs to form an oxidized product.

Other strategies for loading one or more gases into the microtanks are suitable for use with the presently disclosed subject matter, as well. For example, in other embodiments, the gas to be delivered could result from a parent gas, liquid, or solid material that decomposes into the desired gas, e.g., calcium peroxide into oxygen or nitroglycerin into nitric oxide. Encapsulating the parent material in microtank provides another means of loading.

In some embodiments, the microtank further comprises one or more gases loaded in the volume of the one or more vessels under pressure in a hyperbaric environment. In other embodiments, the microtank further comprises one or more gases loaded in the volume of the one or more vessels at a temperature having a range from below 0° C. up to a limiting combustion temperature of the one or more gases or a material comprising the microtank. In still other embodiments, the microtank further comprises one or more gases loaded in the volume of the one or more vessels at a temperature of from about 37° C. to about 100° C. In further embodiments, the microtank further comprises a parent gas, liquid, or solid material capable of decomposing in the gas, thereby releasing the gas in a controlled and sustained manner. In still further embodiments, one or more gases comprise oxygen and the parent gas, liquid, or solid material comprises calcium peroxide. In other embodiments, one or more gases comprise nitric oxide and the parent gas, liquid, or solid material comprises nitroglycerin.

ii. Toward Zero Order and Delayed Release Kinetics

The intrinsic outgassing profile of the presently disclosed microtanks is an exponentially decaying release of gas. This profile is suitable for many applications, for example in oxygen release, where demand decreases over time as angiogenesis and vasculogenesis progresses. For applications where lower order release kinetics are desirable, however, it is possible to tune the microtanks to approximate this release. Given that the driving force of outgassing, the relatively elevated internal partial pressure, is decreasing over time, the gas barrier properties of the microtank also must decrease proportionally over time to achieve lower order kinetics. This change in barrier properties is possible by tuning the bulk and/or surface degradation properties of the microtanks, making them more permeable to the gas over time. By coating the microtanks with a substantially impermeable, but degradable outer layer, it also is possible to have delayed release kinetics. For example, it is known that PVA has oxygen barrier properties that depend on humidity. By coating the PVA layer with a degradable humidity barrier (e.g. PLGA), it is possible to achieve time varying oxygen barrier properties.

The controlled release of gases from the presently disclosed microtanks can be accomplished through various mechanisms. For example, water, or other molecules, can be permeated into the microtank to hydrolyze, or otherwise be involved in, a gas freeing reaction inside the microtank. This strategy would nullify the need for a gas barrier property of the microtanks.

In other embodiments, an activated release strategy can be employed wherein the gas barrier properties of the microtanks can be tuned by application of stimuli including, but not limited to, a magnetic field, an electric field, electromagnetic radiation (e.g., light), a change in pH, a change in temperature, and the like. In still other embodiments, the controlled and sustained release of the one or more gases is activated by an application of a stimulus to the microtank, wherein the stimulus is selected from the group consisting of a magnetic field, an electric field, electromagnetic radiation, a change in pH, a change in temperature, the generation of one or more pinholes in the at least one gas barrier and/or means for mechanical confinement, an imperfection in the at least one gas barrier and/or means for mechanical confinement, a disruption of polymer packing in the at least one gas barrier and/or means for mechanical confinement, and combinations thereof. An activated release strategy also could include the generation of pinholes, imperfections, or a disruption of polymer packing, and the like.

In some embodiments, at least one gas barrier and/or means for mechanical confinement are adapted to release the one or more gases from the volume of the one or more vessels with an outgassing profile having an exponentially decaying release of the one or more gases. In other embodiments, at least one gas barrier and/or means for mechanical confinement are adapted to have one or more gas barrier properties which decrease proportionally over time to provide an outgassing profile having lower order kinetics. In still other embodiments, at least one gas barrier and/or means for mechanical confinement are adapted to have one or more bulk and/or surface degradation properties which are more permeable to the one or more gases over time to provide an outgassing profile having a lower order release kinetics. In further embodiments, at least one gas barrier and/or means for mechanical confinement are coated with a substantially impermeable but degradable outer layer to provide an outgassing profile having a delayed release kinetics.

In some embodiments, the microtank further comprises one or more molecules capable of permeating the volume of the one or more vessels and modifying a gas freeing reaction contained therein to provide an outgassing profile having a modified release kinetics. In other embodiments, one or more molecules comprise water, and the gas freeing reaction comprises a hydrolyzation reaction.

B. Methods of Delivering One or More Gases to a Target

The use of controlled outgassing of hyperbarically loaded materials for the delivery of oxygen and other therapeutic gases in biomedical applications provides numerous advantages over the prior art including, but not limited to, controlling the release profile of gases; the dose of gases; the spatial distribution of gases; and the components of the gases.

These aspects of the presently disclosed subject matter allow for gases to be used in a completely novel and useful manner Currently, using methods known in the art, gases are delivered systemically through ventilation, which limits their therapeutic applications. In contrast, the presently disclosed devices and methods provide for a controllable localization, release profile, and dosage. Accordingly, the therapeutic utility and potential of gases delivered in this way increases greatly, analogous to how the controlled release of proteins and drugs has enhanced their utility.

Several gases have therapeutic properties, including, but not limited to: oxygen, nitric oxide, carbon monoxide, hydrogen, hydrogen sulfide, ozone, xenon, and the like. Many of these gases, however, are not compatible with systemic delivery. The presently disclosed microtanks, however, are compatible with almost all gases, circumvent systemic delivery, and facilitate the clinical use of these gases.

For example, the presently disclosed microtanks could be used to supply oxygen to hypoxic tissue (gas as a metabolic component), nitric oxide to promote vascular dilation (gas as a signaling molecule), or ozone to fight infections (gas as an antimicrobial agent), and the like. In summary, the presently disclosed subject matter provides a controlled delivery system for gases in the body with a breadth of immediate and potential applications.

In some embodiments, the presently disclosed microtanks can be used to provide temporary oxygen supply to developing tissue-engineered constructs. The presently disclosed devices and methods, however, also can be employed in the following representative applications:

i. Plastic Surgery and Transplantations

Every time a piece of tissue is dissected it loses a vital supply of blood and suffers ischemia and hypoxia as a result, thereby impacting surgical outcomes. While tissue flaps mitigate this risk by transplanting with major blood vessels intact and/or reconnecting them afterward through microsurgery, it is impossible to reconnect every vessel and capillary. For tissue grafts, passive diffusion is the only mechanism to receive oxygen for at least the first few days until underlying blood vessels, if present, grow into the ischemic tissue and anastomose. The presently disclosed microtanks could have immediate therapeutic value to the field of plastic surgery by acting as a temporary source of oxygen in these cases. This could be done by injecting the microtanks throughout the tissue or coating the surfaces of thinner samples with the microtanks.

In the context of what constitutes a thin sample, one must consider how far oxygen can diffuse. It is commonly cited that cells must be within approximately 400 μm of a capillary to meet their oxygen demands. This criterion, however, is not entirely true of microtanks. Microtanks have the potential to deliver pure oxygen (approximately 760 mmHg), whereas oxygen in the blood supply is usually between about 21 mmHg to about 57 mmHg. Hence, the gradient driving diffusion is potentially an order of magnitude larger and consequently the critical distance for delivering oxygen from a microtank is roughly an order of magnitude larger, i.e., about 4 mm. This characteristic makes the technology very attractive in a field conducting 10's of millions of surgeries annually in the United States alone.

ii. Ischemic Diseases

Heart attacks, diabetic ulcers, and many other ischemic diseases stem from a loss of oxygen supply to the tissue. This loss of oxygen results in cell death and compromised healing. The rates of myocardial infarction are roughly 750,000 cases per year in the United States alone; further, diabetic ulcers affect around 4 million Americans. In the case of myocardial infarction, muscle loss is a function of time. The presently disclosed microtanks could be injected into the ischemic heart muscle to help prevent cell death and facilitate tissue repair. In the case of diabetic ulcers, oxygen-loaded microtanks could be deposited into a hydrogel and/or products currently used to treat such ulcers and to support wound healing. The local delivery of oxygen using microtanks within an ulcer could provide significant advantages over current hyperbaric oxygen (HBO) therapy where a patient is confined in a hyperbaric chamber and subject to systemic elevated oxygen levels. The use of microtanks could be advantageous in that they would provide continuous delivery of oxygen to the wound site as opposed to HBO therapy which provides only periodic elevated oxygen, commonly in 30-90 minutes sessions. Additionally, the use of localized oxygen delivery with microtanks obviates that need for repeated visits to the clinic as is the case for HBO therapy. Localized delivery mitigates the risks associated with oxygen toxicity and fire—the two greatest risks associated with HBO therapy.

iii. Tissue-Engineered Constructs

The potential of tissue engineering is tremendous, but it is currently limited by challenges of oxygen supply within nascent cellularized constructs. The presently disclosed microtanks can be incorporated into either the hydrogel phase or the scaffold phase of the constructs to act as a temporary oxygen supply to maintain cells while vasculature develops and anastomoses with the host. This temporary supply of oxygen would allow significantly higher initial cell seeding densities and larger constructs to be made. Accordingly, the presently disclosed microtanks could help to bring tissue engineering out of the lab and into the clinic.

One of ordinary skill in the art would recognize upon review of the presently disclosed subject matter that the presently disclosed microtanks can be used in applications other than biomedical applications including, but not limited to, supplying one or more gases to a fuel cell, and the like.

For example, the presently disclosed microtanks and methods of their use can be applied to veterinary uses, for analogous uses as in human subjects; in advanced composite materials, for example, combined as a component of a composite material for added functionality; packaging, for example, for release of gases to maintain product freshness and/or to preserve the product, in a manner similar to tank blanketing approaches; controlled chemical reactions, for example, as a means for delivering gas components of a reaction in a controlled, dispersed/uniform, and potentially reaction limiting manner, which facilitates the addition of multiple types of gases simultaneously; agriculture/aquaculture, for example, for delivery of gases with antimicrobial, signaling, and the like, properties to crops, which could be used to modify the gases in soil or on the surface of leaves or in the aqueous phase; food preservation, for example, for the ripening of fruits by release of ethylene or by release of antimicrobial gases, such as a sulfite to prevent rotting or over ripening; pest control, for example, as a means for dispensing a gaseous agent, such as a nerve gas or agent, for pest control; and sterilization, for example, embedding materials with microtanks loaded with a sterilizing gas to form a sustained film over the surface to prevent bacterial growth.

The subject treated by the presently disclosed methods in their many embodiments is desirably a human subject, although it is to be understood that the methods described herein are effective with respect to all vertebrate species, which are intended to be included in the term "subject."

A "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

Accordingly, in some embodiments, the presently disclosed subject matter provides a method for delivering one or more gases to a target in a controlled and sustained manner, the method comprising: (a) providing a presently disclosed microtank comprising one or more vessels, wherein the one or more vessels have a volume defined by at least one gas barrier and/or a means for mechanical support/confinement, wherein the volume of the one or more vessels is capable of being loaded with one or more gases at an atmospheric pressure or a hyperbaric pressure and subsequently releasing the one or more gases in a controlled and sustained manner; (b) loading the one or more vessels with one or more gases; and (c) releasing the one or more gases to the target in a controlled and sustained manner.

In some embodiments, one or more gases are selected from the group consisting of oxygen, nitric oxide, carbon monoxide, hydrogen, hydrogen sulfide, ozone, xenon, ethylene, a sulfite, and combinations thereof. In other embodiments, one or more gases comprise a metabolic component. In still other embodiments, one or more gases comprise oxygen. In further embodiments, the oxygen is delivered to hypoxic tissue.

In some embodiments, one or more gases comprise a signaling molecule. In other embodiments, the signaling molecule comprises a vasodilator.

In some embodiments, one or more gases comprise nitric oxide. In other embodiments, one or more gases comprise an antimicrobial agent. In still other embodiments, one or more gases comprise ozone.

In some embodiments, the method comprises providing a temporary oxygen supply to a target selected from the group consisting of a developing tissue-engineered construct, a tissue graft, an ischemic heart tissue, and a diabetic ulcer. In other embodiments, the tissue-engineered construct comprises scaffold for regenerating bone tissue, the scaffold comprising a plurality of biodegradable fibers configured to form a porous, three-dimensional (3D) network of fibers, wherein the porous, three-dimensional network of fibers further comprise a hydrogel, and wherein the hydrogel comprises one or more cells encapsulated therein and one or more growth factors capable of promoting regeneration of bone tissue.

In some embodiments, one or more microtanks are incorporated into the hydrogel, the scaffold, and combinations thereof. In other embodiments, the method comprises administering the temporary oxygen supply to the target by a method selected from the group consisting of injecting one or more microtanks into the target, coating a surface of the target with one or more microtanks, disposing one or more microtanks into a medium adapted to treat the target, and combinations thereof.

In some embodiments, the method comprises injecting one or more microtanks into ischemic heart tissue to prevent cell death and/or to facilitate tissue repair. In other embodiments, the method comprises depositing one or more microtanks into a medium adapted to treat a wound. In still other embodiments, the wound comprises a diabetic ulcer.

In some embodiments, the medium comprises a hydrogel.

C. Fabrication Strategies

The presently disclosed microtanks can be fabricated by solution coating with an appropriate polymer, e.g., EVOH, PVOH, and the like; using sacrificial/template microballoons; or by fabrication of the microballoons directly out of the barrier material. Accordingly, the presently disclosed microtanks can be fabricated from the following representative strategies:

i. Microballoons

Several microballoons are commercially available for use as lightweight fillers in syntactic foams and various epoxy applications. Microballoons usually range in size from about 50 µm to about 500 µm, although they can be found significantly larger or smaller. Microballoons can be made from a variety of materials including, but not limited to, phenolic resin, glass, polymers, ceramics, metals, and the like. Microballoons are easily sifted and sorted to achieve a near homogenous population. With numerous manufacturing options for microballoons, custom microballoons of appropriately biocompatible materials also could be made. Microballoons can be used as templates for further coating of appropriate materials.

ii. Microtubing

Various microtubes are commercially available and have diameters ranging from several microns to several millimeters. They can be made from a variety of materials including, but not limited to, glass, polymer, metals, ceramics, and the like. A microtube can be used as a microtank by sealing its ends. The tube release profiles can be varied by varying the aspect ratio. The ends of the tubes can be fused closed or plugged by another material of a specific and desirable gas barrier property to further modulate the release profile.

iii. Microbubbles

Microbubbles can be introduced into the continuous phase of a material through a variety of approaches. For example, monodispersed microbubbles can be generated using microfluidic co-extrusion techniques. Airation of the continuous phase is another approach that can be used and, in representative embodiments, includes melting the material to a liquid and then bubbling gas through it, vigorously stirring, or otherwise introducing microbubbles the liquid and then cooling to a solid state. Additionally, the incorporation and activation of a blowing agent in the material can generate voids.

iv. Emulsions

The core-shell morphology desired in a microtank can be achieved using emulsion strategies. For example, an aqueous solution of PVA can be emulsified in molten PCL by vigorous mixing, injection, coextrusions, or other means. Upon cooling, the material contains solid PCL surrounding droplets of aqueous PVA. By removing the aqueous phase through heating and or vacuum, the PVA forms a coating around the void thus producing a microtank. In a similar approach, a double emulsion can be used to encapsulate aqueous PVA in PLGA, forming PLGA microcapsules of aqueous PVA. Similarly, upon removal of the aqueous phase the PVA coats the inside of the capsule forming a microtank. The formation of such precursor emulsions or double emulsions can be achieved by a number of means such as mechanical agitation in a vessel through stirring or by microfluidic approaches.

The core-shell morphology can also be achieved using interfacial polymerization approaches. Briefly, an oil phase containing a monomer and an aqueous phase containing a complimentary monomer and desired polymer to be encapsulated are formed into an emulsion. By selecting monomer pairs that react with each other to form a polymer, it is possible to generate a polymeric membrane at the interface of the dispersed and continuous phase, effectively encapsulating the contents. This approach is well established for polyurethane chemistry and could be used to encapsulate the oxygen barrier material, which would subsequently coat the inside of the capsule upon evaporation of solvent.

In some embodiments, one or more vessels are selected from the group consisting of a microballoon, a hollow microsphere, a syntactic foam, an emulsion, and a closed-cell structure. In other embodiments, the volume of one or more vessels comprises a gas, a vacuum, a liquid, or a solid. In still other embodiments, one or more gases are selected from the group consisting of a therapeutic agent, a ripening agent, and an antimicrobial agent. In further embodiments, one or more gases are selected from the group consisting of oxygen, nitric oxide, carbon monoxide, hydrogen, hydrogen sulfide, ozone, xenon, ethylene, a sulfite, and combinations thereof.

Accordingly, in some embodiments, the presently disclosed subject matter provides a method for fabricating a microtank for delivering one or more gases in a controlled and sustained manner, the method comprising: (a) providing or preparing one or more vessels, wherein the one or more vessels have a volume defined by at least one gas barrier and/or a means for mechanical support/confinement, wherein the volume of the one or more vessels is capable of being loaded with one or more gases at an atmospheric or a hyperbaric pressure and subsequently releasing the one or more gases in a controlled and sustained manner; and (b) loading the one or more vessels with one or more gases.

In some embodiments, the gas barrier and/or means for mechanical support/confinement comprises a material selected from the group consisting of polyvinyl alcohol (PVOH), ethylene vinyl alcohol (EVOH), polyethylene terephthalate (PET), polycaprolactone (PCL), poly(lactic-co-glycolic acid) (PLGA), poly(lactic acid) (PLA), poly(glycolic acid) (PGA), a biocompatible polymer, a silica coating, a metal coating, a ceramic, and combinations thereof.

In some embodiments, one or more vessels have a dimension ranging from about 1 nanometer to about 1000 millimeters. In other embodiments, one or more vessels have a dimension ranging from about 1 micrometer to about 1000 micrometers.

In some embodiments, the loading of one or more vessels with one or more gases is performed under pressure in a hyperbaric environment. In other embodiments, one or more gases is loaded in the volume of the one or more vessels at a temperature having a range from below 0° C. up to a limiting combustion temperature of the one or more gases or a material comprising the microtank. In still other embodiments, loading of one or more vessels with one or more gases is performed at a temperature of from about 37° C. to about 100° C. In further embodiments, loading of one or more vessels with one or more gases includes a parent gas, liquid, or solid material capable of decomposing in the gas, thereby releasing the gas in a controlled and sustained manner.

In some embodiments, one or more gases comprise oxygen and the parent gas, liquid, or solid material comprises calcium peroxide. In other embodiments, one or more gases comprise nitric oxide and the parent gas, liquid, or solid material comprises nitroglycerin.

In some embodiments, at least one gas barrier and/or means for mechanical confinement are adapted to release one or more gases from the volume of the one or more vessels with an outgassing profile having an exponentially decaying release of the one or more gases. In other embodiments, at least one gas barrier and/or means for mechanical confinement are adapted to have one or more gas barrier properties which decrease proportionally over time to provide an outgassing profile having lower order kinetics. In still other embodiments, at least one gas barrier and/or means for mechanical confinement are adapted to have one or more bulk and/or surface degradation properties which are more permeable to the one or more gases over time to provide an outgassing profile having a lower order release kinetics. In further embodiments, at least one gas barrier and/or means for mechanical confinement are coated with a substantially impermeable but degradable outer layer to provide an outgassing profile having a delayed release kinetics.

In some embodiments, loading of the one or more vessels with one or more gases includes providing one or more molecules capable of permeating the volume of the one or more vessels and modifying a gas freeing reaction contained therein to provide an outgassing profile having a modified release kinetics. In other embodiments, one or more molecules comprise water, and the gas freeing reaction comprises a hydrolyzation reaction.

In some embodiments, the controlled and sustained release of one or more gases is activated by an application of a stimulus to the microtank, wherein the stimulus is selected from the group consisting of a magnetic field, an electric field, electromagnetic radiation, a change in pH, a change in temperature, the generation of one or more pinholes in the at least one gas barrier and/or means for mechanical confinement, an imperfection in the at least one gas barrier and/or means for mechanical confinement, a disruption of polymer packing in the at least one gas barrier and/or means for mechanical confinement, and combinations thereof.

In some embodiments, one or more vessels are selected from the group consisting of a microballoon, a hollow microsphere, a syntactic foam, an emulsion, and a closed-cell structure. In other embodiments, the volume of one or more vessels comprises a gas, a vacuum, a liquid, or a solid. In still other embodiments, one or more gases are selected from the group consisting of a therapeutic agent, a ripening agent, and an antimicrobial agent. In further embodiments, one or more gases is selected from the group consisting of oxygen, nitric oxide, carbon monoxide, hydrogen, hydrogen sulfide, ozone, xenon, ethylene, a sulfite, and combinations thereof.

D. Oxygen and Nitric Oxide/DMOG

The supplementation of oxygen by the presently disclosed microtanks might, under some circumstances, disrupt some of the signaling events that govern vessel growth and development. By combining oxygen with nitric oxide delivery or a hypoxia inducible factor stabilizer (e.g., DMOG (dimethyloxalylglycine, N-(methoxyoxoacetyl)-glycine methyl ester, also referred to as dimethyloxaloylglycine)) it may be possible to "trick" the cells into thinking they are hypoxic and therefore stimulate vessel proliferation without the cells actually suffering from hypoxia/anoxia.

As used herein, the term "hypoxia" refers to a state of insufficient oxygen availability within tissues causing injury and eventual cell death. The term "anoxia" refers to a total depletion in the level of oxygen, an extreme form of hypoxia. Hypoxia is a prominent feature in diabetic foot ulcers, graft transplantations, and in tissue engineering. For example, tissue hypoxia can be a source of complications in skin graft procedures. Further, tissue engineering research is limited by oxygen diffusion to dimensions of mm's.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The descriptions and specific examples that follow are only intended for the purposes of illustration, and are not to be construed as limiting in any manner to make compounds of the disclosure by other methods.

Example 1

Representative Embodiment

To demonstrate that the presently disclosed approach can work in practice, several materials were created with different gas capacities and time courses of release. In these prototype materials, phenolic microballoons or hollow porous silica microspheres were suspended in melted thermoplastics, e.g., polycaprolactone (PCL) and polyethylene terephthalate (PET), to generate void spaces that would serve as the microtanks. The materials were then cast into thin discs (1-mm thick, 1.5-cm diameter). These discs were placed in a custom-built hyperbaric oxygen chamber and loaded with 100% oxygen at 500 psi for 4 days. The discs were then mounted and submerged in a solution of resazurin, NaOH, and glucose and monitored for 5 days. This solution turns colorless in the absence of oxygen, but bright pink in the presence of oxygen, in a colorimetric fashion. It also scavenges free oxygen and rapidly consumes it, thus maintaining an otherwise anoxic environment.

The kinetics of oxygen release from the scaffolds was measured by imaging the presence of a diffuse pink haze around the discs over 5 days. The release kinetics matched very closely with the predicted values from theoretical calculations, with the PCL-based materials releasing over 24 hours and the PET materials still releasing over the 5 days. In another test, the same material, but with different numbers of microtanks, was tested and the results suggested similar release kinetics. The results also suggest a total gas release proportional to the number of microtanks.

Example 2

Potential Applications

The most generally applicable product(s) would be a line of microtanks with designated release kinetics and profiles, as well as degradation characteristics to span the therapeutic applications from longer releases for tissue engineering to more rapid release for cardiac infarctions. This implementation allows a single line of microtanks to serve a variety of fields and applications. For example, the loaded microtanks could be easily mixed into a hydrogel product before injection or mixed into a printable/castable scaffold material. See, for example, FIG. 4, which illustrates an application of the presently disclosed subject matter to bone tissue engineering scaffolds comprising a PCL phase and a hydrogel phase, whereby the presently disclosed microtanks are embedded in the PCL phase and oxygen outgasses into the hydrogel phase.

The scaffold for regenerating bone tissue can comprise a plurality of biodegradable fibers configured to form a porous, three-dimensional (3D) network of fibers, wherein the porous, three-dimensional network of fibers further comprise a hydrogel, and wherein the hydrogel comprises one or more cells encapsulated therein and one or more growth factors capable of promoting regeneration of bone tissue.

By combining microtanks with different release profiles it is possible to approximate complex release profiles; it also is possible to deliver multiple gases with their own release kinetics. Essentially, the presently disclosed subject matter provides a generic means of delivering therapeutic gases in substantial quantities in a spatially and temporally controlled manner.

Example 3

Oxygen Release Experiment

Referring now to FIG. 1, phenolic microballoons or hollow porous silica microspheres were suspended in melted thermoplastics, in this example, polycaprolactone (PCL) and polyethylene terephthalate (PET), to generate void spaces that would serve as microtanks, as defined herein. The materials were then cast into thin discs (1-mm thick, 1.5-cm diameter). These discs were placed in a custom-built hyperbaric oxygen chamber and loaded with 100% oxygen at 500 psi for 4 days. The discs were then mounted and submerged in a solution of resazurin, NaOH, and glucose and monitored for 5 days. Referring once again to FIG. 1, are shown photographs of oxygen releasing scaffolds in resazurin solution, with pink indicating the presence of oxygen (visible at liquid surface exposed to air and around scaffolds).

Example 4

Fabrication of Biodegradable Microtanks

Biodegradable microtanks can be fabricated by a number of techniques including, but not limited to, double emulsions, single emulsions, interfacial polymerization, microfluidic approaches, and the like. As provided herein below, in some embodiments, a double emulsion approach is used to fabricate the presently disclosed microtanks. Using a double emulsion approach, microtanks having a shell comprising two concentric layers of PLGA (exterior) and PVA (interior) can be fabricated. Both polymers were selected for their biodegradability and biocompatibility properties. The water barrier properties of the PLGA layer reduce the hydration of the PVA layer, which is known to have reduced oxygen barrier properties at elevated humidity. By tuning the ratio of lactic and glycolic acid it is possible to control the degradation rate of the PLGA layer and thereby control the biodegradation of the microtanks. Once the PLGA layer is broken, the hydration of the PVA layer leads to dissolution of the PVA and clearance from the body. Accordingly, in some embodiments, the period of degradation of the PLGA is matched to the period of oxygen release from the microtanks.

In particular embodiments of the presently disclosed double emulsion approach, 0.5 mL of 20% W/V PVA in water were added to 0.5 g PLGA in dichloromethane. The immiscible solutions were emulsified using a sonicator at 10 W for 30 seconds before being quickly poured into a 1000-mL beaker containing 300 mL of 0.1% W/V PVA in water, which was stirred at 300 rpm and was at room temperature, to form the second emulsion. The dichloromethane was gradually evaporated over 3 hours and the resulting particles were collected. The particles were washed 3× using distilled water and then dried under vacuum for 3 days. Examination of the particles under a light microscope revealed a hollow core-shell morphology of PLGA (exterior), PVA (interior), encapsulating a hollow core.

Such an approach is amenable to microfluidic methods, which provide greater control over the shape and size of the particles. The thickness of the PVA coating can be increased by increasing the size of the PVA droplets during the primary emulsion or by increasing the percentage of PVA in the initial solution.

Example 5

3D Printed Bone Scaffolds with Microtanks

The microscopic dimensions of the presently disclosed microtanks allow them to be combined with PCL or other thermoplastics for extrusion and 3D printing applications (see FIG. 5). Such technologies could allow the judicial placement of microtanks throughout a scaffold to achieve specific 3D oxygen profiles. Release of oxygen from microtank containing scaffolds is demonstrated (FIG. 5, right) using a colorimetric dye, resazurin.

Example 6

Biological Efficacy

Adipose-derived stem cells were seeded at 2,500 cells/µL in 100-µL fibrin gels onto microtank-filled scaffolds. Cells were cultured at 37° C. in anoxic chambers (0% $O_2$, 5% $CO_2$) for 6 days to simulate the post-transplantation environment. Positive controls were cultured at 20% $O_2$, 5% $CO_2$. Scaffolds containing the presently disclosed microtanks (1:8 by volume) were loaded to 5 atm with oxygen for 2 weeks. In this embodiment, the scaffolds were composed of acrylonitrile microballoons mixed into molten PCL and cast into 3-mm thick×8-mm diameter discs. Scaffolds were allowed to degas for 3, 2, and 1 days prior to cell seeding resulting in different amounts of oxygen delivery to cells (low, medium, high, respectively); the negative control was loaded with nitrogen at 1 atm.

Maintained Cell Health.

Referring now to FIG. 6, results of an Alamar blue assay demonstrate that normative cell metabolism can be maintained in anoxic environments through microtank oxygen supply. This characteristic is important to achieving predictable cell behavior in vivo.

Enhanced Cell Viability and Morphology.

Referring now to FIG. 7, live (light gray)/Dead (dark gray) fluorescence images highlight the ability of microtank oxygen augmentation to maintain cell viability in anoxic environments. Note the healthy, elongated morphology (left) versus the dying, balled up morphology (right).

Further, oxygen augmentation in TE'd orthopedic grafts using microtank technology maintains cell viability during period of blood vessel ingrowth. This characteristic will enable the introduction of cellularized scaffolds into clinical practice.

Enhanced Cell Proliferation.

Referring now to FIG. 8, quantification of changes in DNA highlight the ability of Microtanks to enable robust cell expansion within anoxic environments. It is important to match delivery rates to cellular demand for optimal benefit.

Enhanced Blood Vessel Formation.

Referring now to FIGS. 9A and 9B, immunostaining of blood vessel marker CD31 demonstrates significantly greater vessel formation with Microtank oxygen augmentation (A). Vessels can be seen sprouting throughout the fibrin gel (B), which is critical for the long term viability of the graft.

Summary.

From these biological results it can be seen that it is important to match the rate of oxygen delivery to the demands of the cells. Excess oxygen delivery can compromise cells due to oxygen toxicity where as insufficient oxygen can compromise cells due to hypoxia. The ability to tune the release profiles of microtanks is therefore useful in biological applications.

Example 7

Derivation of Governing Equations for Core-Shell Spherical Microtanks

P=Pressure
V=Volume of Microtank
n=moles of gas
R=Ideal gas constant
T=temperature
σ=Oxygen permeability
A=Microtank surface area
r=Microtank radius
d=Microtank shell thickness
$E_p$=Activation energy of permeation of oxygen through shell Ideal Gas Law:

$$PV = nRT \quad \dot{n} = \frac{\dot{P}V}{RT}$$

Permeation of Gas Through a Polymer Membrane:

$$\dot{n} = \frac{-\sigma \cdot \Delta P \cdot A}{d} \quad \Delta P = P - P_{O_2 atm} \approx P$$

Geometry Considerations for Spherical System:

$$A = 4\pi r^2 \quad V = 4/3\pi r^3$$

Combining Ideal Gas Law and Permeation Through a Polymer Membrane:

$$\frac{\dot{P}V}{RT} = \frac{-\sigma \cdot \Delta P \cdot A}{d}$$

$$\dot{P} = \frac{-\sigma \cdot P \cdot A \cdot RT}{d \cdot V}$$

$$\dot{P} = \frac{-\sigma \cdot P \cdot 4\pi r^2 \cdot RT}{d \cdot 4/3\pi r^3}$$

$$\dot{P} = \frac{-3 \cdot \sigma \cdot P \cdot RT}{d \cdot r}$$

$$\int \frac{dP}{P} = \int \frac{-3 \cdot \sigma \cdot RT}{d \cdot r} dt$$

$$\ln(P) = \frac{-3 \cdot \sigma \cdot RT}{d \cdot r} t + \ln(P_0)$$

$$P(t) = P_0 \exp\left(\frac{-3 \cdot \sigma \cdot RT}{d \cdot r} t\right)$$

$$P(t) = P_0 \exp\left(\frac{-t}{\tau}\right), \text{ where } \tau = \frac{d \cdot r}{3 \cdot \sigma \cdot RT}$$

$$P(t) = \frac{P_0}{\tau} \exp\left(\frac{-t}{\tau}\right)$$

$$\dot{n}(t) = \frac{VP_0}{RT\tau} \exp\left(\frac{-t}{\tau}\right) = \frac{n_0}{\tau} \exp\left(\frac{-t}{\tau}\right)$$

$$ODR = \frac{\rho\left(\frac{VP_0}{RT}\right)}{\tau} \exp\left(\frac{-t}{\tau}\right) = \frac{\rho(4\pi r^2 P_0)\sigma}{d} \exp\left(\frac{-t}{\frac{d \cdot r}{3 \cdot \sigma \cdot RT}}\right)$$

$$ODR = \frac{\rho(4\pi r^2 P_0)\sigma}{d} \exp\left(\frac{-t}{\frac{d \cdot r}{3 \cdot \sigma \cdot RT}}\right), \text{ where } \tau = \frac{d \cdot r}{3 \cdot \sigma \cdot RT}$$

Effect of Temperature on Permeation:

$$\tau = \frac{d \cdot r}{3 \cdot \sigma_0 \exp\left(\frac{-E_p}{RT}\right) \cdot RT}$$

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

U.S. Pat. No. 8,377,555 for "Gas Storage Materials, Including Hydrogen Storage Materials," to Mohtadi, R. F., et al, issued Feb. 19, 2013;

International PCT Patent Application Publication No. 2009018269 A1 for "Microtanks for Compressed Gas Storage and Methods for Making Same," to Long, X., published Feb. 5, 2009;

U.S. Pat. No. 7,198,867 B2, for "Electrochemical Generation, Storage and Reaction of Hydrogen and Oxygen," to Sanders, N. A., issued Apr. 3, 2007;

U.S. Pat. No. 7,105,151, for Oxygen Delivery Agents and Uses for the Same, to Unger, E. C., et al., issued Sep. 12, 2006; and U.S. Pat. No. 4,842,620, for "Process of Gas Enrichment with Porous Siliceous-Containing Material," to Hammell, J. J., et al., issued Jun. 27, 1989. ADD more citations and patents Although the foregoing subject matter has been described in some detail by way of illustration and example for purposes of clarity of understanding, it will be understood by That which is claimed:

1. A scaffold comprising a polymeric material having embedded in a continuous phase thereof one or more microtanks, the one or more microtanks having a hollow core-shell morphology having an exterior comprising a polymeric material selected from the group consisting of polyethylene terephthalate (PET), polycaprolactone (PCL), poly(lactic-co-glycolic acid) (PLGA), poly(lactic acid) (PLA), and poly(glycolic acid) (PGA), and an interior comprising a material selected from the group consisting of polyvinyl alcohol (PVOH), ethylene vinyl alcohol (EVOH), a phenolic resin, and porous silica, wherein the interior of the core-shell comprises a void having a shape of a microbubble, a microballoon, a microsphere, or a microtube, wherein the void comprises one or more gases at a hyperbaric pressure and has a spherical shape having a diameter ranging from about 1 nanometer to about 1000 micrometers.

2. The scaffold of claim 1, wherein the void has a spherical shape having a diameter ranging from about 1 micrometer to about 1000 micrometers.

3. The scaffold of claim 1, wherein the one or more gases are selected from the group consisting of a therapeutic agent, a ripening agent, and an antimicrobial agent.

4. The scaffold of claim 3, wherein the one or more gases are selected from the group consisting of oxygen, nitric oxide, carbon monoxide, hydrogen, hydrogen sulfide, ozone, xenon, ethylene, a sulfite, and combinations thereof.

5. The scaffold of claim 1, wherein the scaffold further comprises a plurality of biodegradable fibers configured to form a porous, three-dimensional (3D) network of fibers.

6. The scaffold of claim 5, further comprising a hydrogel phase.

* * * * *